US005998440A

United States Patent [19]

Castro Pineiro et al.

[11] Patent Number: 5,998,440

[45] Date of Patent: Dec. 7, 1999

[54] AZETIDINE, PYRROLIDINE AND PIPERIDINE DERIVATIVES

[75] Inventors: Jose Luis Castro Pineiro; Angus Murray MacLeod, both of Bishops Stortford; Monique Bodil Van Niel, Welwyn Garden City, all of United Kingdom

[73] Assignee: Merck Sharpe & Dohme Ltd., Hoddesdon, United Kingdom

[21] Appl. No.: 09/068,620

[22] PCT Filed: Nov. 13, 1996

[86] PCT No.: PCT/GB96/02764

§ 371 Date: May 8, 1998

§ 102(e) Date: May 8, 1998

[87] PCT Pub. No.: WO97/18201

PCT Pub. Date: May 22, 1997

[30] Foreign Application Priority Data

Nov. 14, 1995 [GB] United Kingdom .................. 9523243

[51] Int. Cl.$^{6}$ ...................... A61K 31/445; C07D 401/06

[52] U.S. Cl. ......................... 514/323; 546/201; 546/199; 546/198; 546/197

[58] Field of Search .................................... 546/201, 196, 546/197, 198, 199; 514/323, 320, 321

[56] References Cited

U.S. PATENT DOCUMENTS

| | | | |
|---|---|---|---|
| 5,576,336 | 11/1996 | Baker et al. | 514/323 |
| 5,854,268 | 12/1998 | Baker et al. | 514/383 |

FOREIGN PATENT DOCUMENTS

| | | |
|---|---|---|
| 94/02477 | 2/1994 | WIPO . |
| 94/21627 | 9/1994 | WIPO . |
| 94/24105 | 10/1994 | WIPO . |
| 96/04274 | 2/1996 | WIPO . |

*Primary Examiner*—Alan L. Rotman
*Assistant Examiner*—Charanjit S. Aulakh
*Attorney, Agent, or Firm*—James L. McGinnis; David L. Rose; Philippe L. Durette

[57] ABSTRACT

A class of substituted azetidine, pyrrolidine and piperidine derivatives, linked by a fluoro-substituted alkylene chain to a fused bicyclic heteroaromatic moiety such as indolyl, are selective agonists of 5-HT$_1$-like receptors, being potent agonists of the human 5-HT$_{1D\alpha}$ receptor subtype while possessing at least a 10-fold selective affinity for the 5-HT$_{1D\alpha}$ receptor subtype relative to the 5-HT$_{1D\beta}$ subtype; they are therefore useful in the treatment and/or prevention of clinical conditions, in particular migraine and associated disorders, for which a subtype-selective agonist of 5-HT$_{1D}$ receptors is indicated, while eliciting fewer side-effects, notably adverse cardiovascular events, than those associated with non-subtype-selective 5-HT$_{1D}$ receptor agonists.

11 Claims, No Drawings

AZETIDINE, PYRROLIDINE AND PIPERIDINE DERIVATIVES

This application is 371 of PCT/GB96/02764 filed Nov. 13, 1996, now WO 97/18201, published May 22, 1997.

The present invention relates to a class of substituted azetidine, pyrrolidine and piperidine derivatives which act on 5-hydroxytryptamine (5-HT) receptors, being selective agonists of so-called "$5-HT_1$-like" receptors. They are therefore useful in the treatment of clinical conditions for which a selective agonist of these receptors is indicated.

It has been known for some time that $5-HT_1$-like receptor agonists which exhibit selective vasoconstrictor activity are of use in the treatment of migraine (see, for example, A. Doenicke et al., *The Lancet,* 1988, Vol. 1, 1309–11; and W. Feniuk and P. P. A. Humphrey, *Drug Development Research,* 1992, 26, 235–240).

The human $5-HT_1$-like or $5-HT_{1D}$ receptor has recently been shown by molecular cloning techniques to exist in two distinct subtypes. These subtypes have been termed $5-HT_{1D\alpha}$(or $5-HT_{1D-1}$) and $5-HT_{1D\beta}$(or $5-HT_{1D-2}$), and their amino acid sequences are disclosed and claimed in WO-A-91/17174.

The $5-HT_{1D\alpha}$ receptor subtype in humans is believed to reside on sensory terminals in the dura mater. Stimulation of the $5-HT_{1D\alpha}$ subtype inhibits the release of inflammatory neuropeptides which are thought to contribute to the headache pain of migraine. The human $5-HT_{1D\beta}$ receptor subtype, meanwhile, is located predominantly on the blood vessels and in the brain, and hence may play a part in mediating constriction of cerebral and coronary arteries, as well as CNS effects.

Administration of the prototypical $5-HT_{1D}$ agonist sumatriptan (GR43175) to humans is known to give rise at therapeutic doses to certain adverse cardiovascular events (see, for example, F. Willett et al., *Br. Med. J.,* 1992, 304, 1415; J. P. Ottervanger et al., *The Lancet,* 1993, 341, 861–2; and D. N. Bateman, *The Lancet,* 1993, 341, 221–4). Since sumatriptan barely discriminates between the human $5-HT_{1D\alpha}$ and $5-HT_{1D\beta}$ receptor subtypes (cf. WO-A-91/17174, Table 1), and since it is the blood vessels with which the $5-HT_{1D\beta}$ subtype is most closely associated, it is believed that the cardiovascular side-effects observed with sumatriptan can be attributed to stimulation of the $5-HT_{1D\beta}$ receptor subtype. It is accordingly considered (cf. G. W. Rebeck et al., *Proc. Natl. Acad. Sci. USA,* 1994, 91, 3666–9) that compounds which can interact selectively with the $5-HT_{1D\alpha}$ receptor subtype, whilst having a less pronounced action at the $5-HT_{1D\beta}$ subtype, might be free from, or at any rate less prone to, the undesirable cardiovascular and other side-effects associated with non-subtype-selective $5-HT_{1D}$ receptor agonists, whilst at the same time maintaining a beneficial level of anti-migraine activity.

The compounds of the present invention, being selective $5-HT_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human $5-HT_{1D\alpha}$ receptor subtype. Moreover, the compounds in accordance with this invention have been found to possess at least a 10-fold selective affinity for the $5-HT_{1D\alpha}$ receptor subtype relative to the $5-HT_{1D\beta}$ subtype, and they can therefore be expected to manifest fewer side-effects than those associated with non-subtype-selective $5-HT_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of $5-HT_1$-like receptors, and accordingly to be of particular use in the treatment of migraine and associated conditions. None of these publications, however, discloses nor even suggests the azetidine, pyrrolidine and piperidine derivatives provided by the present invention.

In EP-A-0548813 is described a series of alkoxypyridin-4yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the precisely substituted piperazine moiety described therein with a differently substituted azetidine, pyrrolidine or piperidine moiety; nor is there any suggestion therein that the alkylene chain present in the indol-3-ylalkylpiperazine portion of the molecule might be substituted with one or more fluorine atoms.

WO-A-91/18897 describes a class of tryptamine derivatives substituted by various five-membered rings, which are stated to be specific to a particular type of "$5-HT_1$-like" receptor and thus to be effective agents for the treatment of clinical conditions, particularly migraine, requiring this activity. A further class of tryptamine derivatives with alleged anti-migraine activity is disclosed in WO-A-94/02460. However, neither WO-A-91/18897 nor WO-A-94/02460 discloses or suggests the azetidine, pyrrolidine and piperidine derivatives provided by the present invention.

Moreover, nowhere in the prior art mentioned above is there any disclosure of a subtype-selective $5-HT_{1D}$ receptor agonist having a $5-HT_{1D\alpha}$ receptor binding affinity ($IC_{50}$) below 50 nM and at least a 10-fold selective affinity for the $5-HT_{1D\alpha}$ receptor subtype relative to the $5-HT_{1D\beta}$ subtype.

The compounds according to the present invention are subtype-selective $5-HT_{1D}$ receptor agonists having a human $5-HT_{1D\alpha}$ receptor binding affinity ($IC_{50}$) below 50 nM, typically below 10 nM and preferably below 1 nM; and at least a 10-fold selective affinity, typically at least a 50-fold selective affinity and preferably at least a 100-fold selective affinity, for the human $5-HT_{1D\alpha}$ receptor subtype relative to the $5-HT_{1D\beta}$ subtype. Moreover, the compounds in accordance with this invention possess interesting properties in terms of their efficacy and/or bioavailability.

The present invention provides a compound of formula I, or a salt or prodrug thereof:

(I)

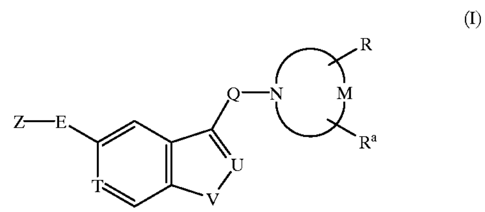

wherein

Z represents hydrogen, halogen, cyano, nitro, trifluoromethyl, —$OR^5$, —$OCOR^5$, —$OCONR^5R^6$, —$OCH_2CN$, —$OCH_2CONR^5R^6$, —$SR^5$, —$SOR^5$, —$SO_2R^5$, —$SO_2NR^5R^6$, —$NR^5R^6$, —$NR^5COR^6$, —$NR^5CO_2R^6$, —$NR^5SO_2R^6$, —$COR^5$, —$CO_2R^5$, —$CONR^5R^6$, or a group of formula (Za), (Zb), (Zc) or (Zd):

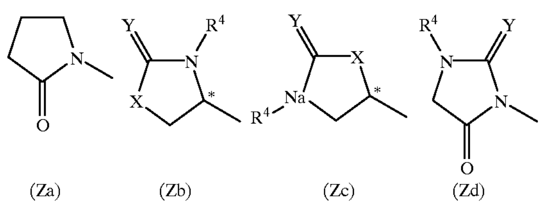

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, substituted in any position by one or more fluorine atoms;

T represents nitrogen or CH;

U represents nitrogen or C—$R^2$;

V represents oxygen, sulphur or N—$R^3$;

$R^2$, $R^3$ and $R^4$ independently represent hydrogen or $C_{1-6}$ alkyl;

$R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring;

M represents the residue of an azetidine, pyrrolidine or piperidine ring;

R represents a group of formula —W—$R^1$;

W represents a chemical bond or a straight or branched alkylene chain containing from 1 to 4 carbon atoms, optionally substituted in any position by a hydroxy group;

$R^1$ represents —$OR^x$, —$SR^x$, —$SOR^x$, —$SO_2R^x$ or —$NR^xR^y$;

$R^x$ and $R^y$ independently represent hydrogen, hydrocarbon or a heterocyclic group; or $R^x$ and $R^y$ together represent a $C_{2-6}$ alkylene group, which alkylene group may be optionally substituted by one or more substituents selected from $C_{1-6}$ alkyl, aryl and hydroxy, or fused with a phenyl ring; and $R^a$ represents hydrogen, hydroxy, hydrocarbon or a heterocyclic group.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl.

When $R^5$ and $R^6$, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl($C_{1-6}$)alkyl, $C_{1-6}$ alkoxy, $C_{2-6}$ alkoxycarbonyl and $C_{1-6}$ alkylaminocarbonyl. Typical substituents include methyl, benzyl, methoxy, methoxycarbonyl, ethoxycarbonyl and methylaminocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-6}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $—NR^vR^w$, $—NR^vCOR^w$, $—NR^vCO_2R^w$, $—NR^vSO_2R^w$, $—CH_2NR^vSO_2R^w$, $—NHCONR^vR^w$, $—CONR^vR^w$, $—SO_2NR^vR^w$ and $—CH_2SO_2NR^vR^w$, in which $R^v$ and $R^w$ independently represent hydrogen, $C_{1-6}$ alkyl, aryl or aryl ($C_{1-6}$)alkyl, or $R^v$ and $R^w$ together represent a $C_{2-6}$ alkylene group.

When $R^x$ and $R^y$, or $R^v$ and $R^w$, together represent a $C_{2-6}$ alkylene group, this group may be an ethylene, propylene, butylene, pentamethylene or hexamethylene group, preferably butylene or pentamethylene.

When $R^x$ and $R^y$ together represent a $C_{2-6}$ alkylene group, this group may be unsubstituted or substituted by one or more substituents selected from $C_{1-6}$ alkyl, aryl and hydroxy. Typical substituents include methyl, phenyl and hydroxy.

Furthermore, when $R^x$ and $R^y$ together represent a $C_{2-6}$ alkylene group, this group may optionally be fused with a phenyl ring. In this context, a typical group of formula $—NR^xR^y$ as defined for the substituent $R^1$ is 1,2,3,4-tetrahydroisoquinolinyl.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs,* ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. For example, the compounds of formula I above wherein Z represents a group of formula (Zb) or (Zc) have a chiral centre denoted by the asterisk *, which may accordingly be in the (R) or (S) configuration. It is to be understood that all such isomers and mixtures thereof in any proportion are encompassed within the scope of the present invention.

In particular, where M represents the residue of a pyrrolidine ring, and the substituent R is attached to the 2-position thereof, then the absolute stereochemical configuration of the carbon atom at the point of attachment of the moiety R is preferably as depicted in structure IA as follows:

(IA)

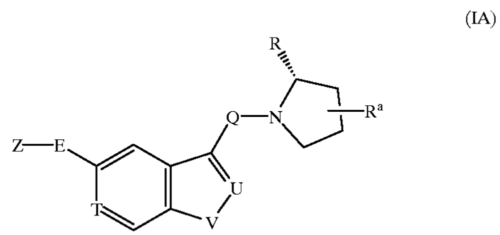

wherein Z, E, Q, T, U, V, R and $R^a$ are as defined above.

Moreover, where M represents the residue of a pyrrolidine ring, and the substituent R is attached to the 3-position thereof, then the absolute stereochemical configuration of the carbon atom at the point of attachment of the moiety R is preferably as depicted in structure IB as follows:

(IB)

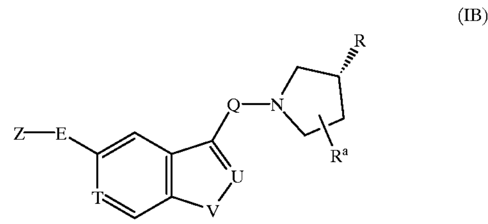

wherein Z, E, Q, T, U, V, R and $R^a$ are as defined above.

Where E and W, which may be the same or different, represent straight or branched alkylene chains, these may be, for example, methylene, ethylene, 1-methylethylene, propylene, 2-methylpropylene or butylene. In addition, W may be substituted in any position by a hydroxy group giving rise, for example, to a hydroxymethyl-methylene, 2-hydroxypropylene or 2-hydroxymethyl-propylene linkage. Moreover, E and W may each independently represent a chemical bond. Where E represents a chemical bond, the moiety Z is attached directly to the central fused bicyclic heteroaromatic ring system containing the variables T, U and V. Similarly, where W represents a chemical bond, the substituent $R^1$ is attached directly to the azetidine, pyrrolidine or piperidine ring of which M is the residue.

Suitably, E represents a chemical bond or a methylene linkage.

The alkylene chain Q is substituted in any position by one or more fluorine atoms, preferably by one or two fluorine atoms and more preferably by one fluorine atom. Representative alkylene chains for Q include 2-fluoropropylene, 2,2-difluoropropylene and 2-fluoromethyl-propylene, especially 2-fluoropropylene or 2-fluoromethyl-propylene.

The compound of formula I in accordance with the present invention is suitably an indole, benzofuran or benzthiophene derivative of formula IC, an indazole derivative of formula ID, or a pyrrolo[2,3-c]-pyridine derivative of formula IE:

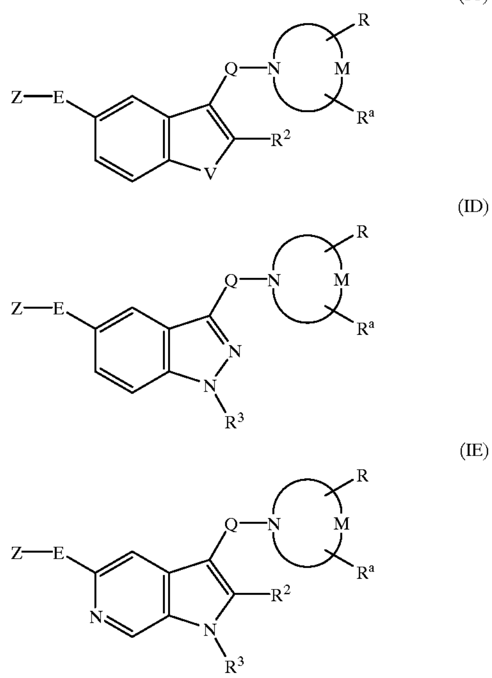

wherein Z, E, Q, V, M, R, $R^a$, $R^2$ and $R^3$ are as defined above. Preferably, the compounds according to the invention are indole or pyrrolo[2,3-c]-pyridine derivatives of formula IF:

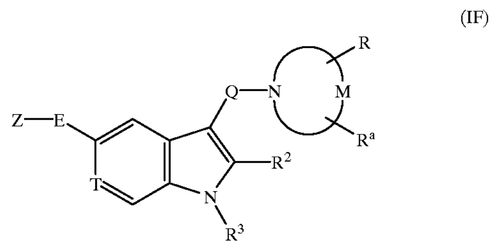

wherein Z, E, Q, T, M, R, $R^a$, $R^2$ and $R^3$ are as defined above, in particular wherein $R^2$ and $R^3$ are both hydrogen.

Suitably, W represents a chemical bond or a methylene or hydroxymethyl-methylene linkage, in particular a chemical bond or a methylene linkage.

Suitably, $R^x$ and $R^y$ independently represent hydrogen, $C_{1-6}$ alkyl, $C_{2-6}$ alkenyl, $C_{3-7}$ cycloalkyl($C_{1-6}$)alkyl, indanyl, aryl, aryl($C_{1-6}$)alkyl, heteroaryl or heteroaryl($C_{1-6}$)alkyl, any of which groups may be optionally substituted by one or more substituents selected typically from $C_{1-6}$ alkyl, halogen, hydroxy, $C_{1-6}$ alkoxy, aminocarbonyloxy, amino, $C_{2-6}$ alkylcarbonylamino, $C_{1-6}$ alkylsulphonylamino and $C_{1-6}$ alkylaminosulphonylmethyl. Particular values of $R^x$ and $R^y$ include hydrogen, methyl, hydroxyethyl, isobutyl, 2,2-dimethylpropyl, allyl, dimethylallyl, 1-cyclohexylethyl, 2-cyclohexylethyl, indanyl, hydroxy-indanyl, phenyl, benzyl, methyl-benzyl, fluorobenzyl, methoxy-benzyl, acetylamino-benzyl, 1-phenylethyl, 2-phenylethyl, 2-hydroxy-1-phenylethyl, 2-methoxy-1-phenylethyl, 2-aminocarbonyloxy-1-phenylethyl, 1-(fluorophenyl)ethyl, 1-(fluorophenyl)-2-hydroxyethyl, 1-(fluorophenyl)-2-methoxyethyl, 1-(acetylamino-phenyl)ethyl, 2-(acetylamino-phenyl)ethyl, 2-hydroxy-1-phenylprop-1-yl, 1-phenylprop-2-yl, 2-phenylprop-2-yl, 1-hydroxy-1-phenylprop-2-yl, 1-hydroxy-2-phenylprop-2-yl, 1-hydroxy-3-phenylprop-2-yl, furylmethyl, thienylmethyl and pyridylmethyl, especially hydrogen, methyl, benzyl or 1-(fluorophenyl)-2-hydroxyethyl.

In addition, where $R^x$ and $R^y$ together represent an optionally substituted or phenyl ring-fused $C_{2-6}$ alkylene group, the substituent —$NR^xR^y$ as defined for $R^1$ may suitably represent 3,3-dimethylpiperidinyl, 2-phenylpiperidinyl, 3-hydroxy-2-phenylpiperidinyl or 1,2,3,4-tetrahydroisoquinolin-2-yl.

Suitable values for the substituent $R^1$ include hydroxy, benzyloxy, methoxy-benzyloxy, pyridylmethoxy, benzylthio, fluorobenzyl-thio, phenylsulphinyl, benzylsulphinyl, fluorobenzyl-sulphinyl, fluorobenzyl-sulphonyl, amino, methylamino, indanylamino, hydroxyindanyl-amino, benzylamino, N-(methylbenzyl)-amino, N-(acetylamino-benzyl)-amino, N-(1-phenylethyl)-amino, N-(2-phenylethyl)-amino, N-(2-hydroxy-1-phenylethyl)-amino, N-(2-methoxy-1-phenylethyl)-amino, N-(2-aminocarbonyloxy-1-phenylethyl)-amino, N-[1-(fluorophenyl)ethyl]-amino, N-[1-(fluorophenyl)-2-hydroxyethyl]-amino, N-[1-(fluorophenyl)-2-methoxyethyl]-amino, N-[1-(acetylamino-phenyl)ethyl]-amino, N-[2-(acetylamino-phenyl)ethyl]-amino, N-(2-hydroxy-1-phenylprop-1-yl)-amino, N-(1-phenylprop-2-yl)-amino, N-(2-phenylprop-2-yl)-amino, N-(1-hydroxy-1-phenylprop-2-yl)-amino, N-(1-hydroxy-2-phenylprop-2-yl)-amino, N-(1-hydroxy-3-phenylprop-2-yl)-amino, N-(furylmethyl)-amino, N-(pyridylmethyl)-amino, dimethylamino, N-isobutyl-N-methylamino, N-(2,2-dimethylpropyl)-N-methylamino, N-allyl-N-methylamino, N-(3,3-dimethylprop-2-en-1-yl)-N-methylamino, N-(1-cyclohexylethyl)-N-methylamino, N-benzyl-N-methylamino, N-methyl-N-(methylbenzyl)-amino, N-(fluorobenzyl)-N-methylamino, N-(acetylamino-benzyl)-N-methylamino, N-methyl-N-(1-phenylethyl)-amino, N-methyl-N-(2-phenylethyl)-amino, N-(2-hydroxy-1-phenylethyl)-N-methylamino, N-(2-methoxy-1-phenylethyl)-N-methylamino, N-[2-(acetylamino-phenyl) ethyl]-N-methylamino, N-(furylmethyl)-N-methylamino, N-methyl-N-(thienylmethyl)-amino, N-benzyl-N-(2-hydroxyethyl)-amino, N,N-bis(furylmethyl)-amino, 3,3-dimethylpiperidinyl, 2-phenylpiperidinyl, 3-hydroxy-2-phenylpiperidinyl and 1,2,3,4-tetrahydroisoquinolin-2-yl.

Particular examples of $R^1$ include benzyloxy, N-[1-(fluorophenyl)-2-hydroxyethyl]-amino and N-benzyl-N-methylamino.

Representative values of the group R include hydroxy, benzyloxy, benzyloxymethyl, methoxy-benzyloxy, pyridylmethoxy, benzylthio-methyl, fluorobenzylthio-methyl, phenylsulphinylmethyl, benzylsulphinylmethyl, fluorobenzyl-sulphinyl, fluorobenzyl-sulphinylmethyl, fluorobenzyl-sulphonylmethyl, indanylamino, indanylaminomethyl, hydroxyindanyl-amino, benzylamino, benzylaminomethyl, 1-(N-benzylamino)-2-hydroxyethyl, N-(methylbenzyl)-aminomethyl, N-(acetylamino-benzyl)-amino, N-(acetylamino-benzyl)-aminomethyl, N-(1-phenylethyl)-amino, N-(1-phenylethyl)-aminomethyl, N-(2-phenylethyl)-aminomethyl, N-(2-hydroxy-1-phenylethyl)-amino, N-(2-hydroxy-1-phenylethyl)-aminomethyl, N-(2-methoxy-1-phenylethyl)-amino, N-(2-aminocarbonyloxy-1-phenylethyl)-amino, N-[1-(fluorophenyl)ethyl]-amino, N-[1-(fluorophenyl)-2-hydroxyethyl]-amino, N-[1-(fluorophenyl)-2-methoxyethyl]-amino, N-[1-(acetylamino-phenyl)ethyl]-amino, N-[1-(acetylamino-phenyl)ethyl]-aminomethyl, N-[2-(acetylamino-phenyl)ethyl]-amino, N-(2-hydroxy-1-phenylprop-1-yl)-amino, N-(1-phenylprop-2-yl)-amino, N-(2-phenylprop-2-yl)-aminomethyl, N-(1-hydroxy-1-phenylprop -2-yl)-amino, N-(1-hydroxy-2-phenylprop-2-yl)-amino, N-(1-hydroxy-3-phenylprop-2-yl)-amino, N-(furylmethyl)-amino, N-(furylmethyl)-aminomethyl, N-pyridylmethyl)-aminomethyl, N-isobutyl-N-methyl-aminomethyl, N-(2,2-dimethylpropyl)-N-methyl-aminomethyl, N-allyl-N-methylamino, N-(3,3-dimethylprop-2-en-1-yl)-N-methylamino, N-(1-cyclohexylethyl)-N-methyl-aminomethyl, N-benzyl-N-methylamino, N-benzyl-N-methyl-aminomethyl, N-methyl-N-(methylbenzyl)-aminomethyl, N-(fluorobenzyl)-N-methylamino, N-(acetylamino-benzyl)-N-methyl-aminomethyl, N-methyl-N-(1-phenylethyl)-aminomethyl, N-methyl-N-(2-phenylethyl)-aminomethyl, N-(2-hydroxy-1-phenylethyl)-N-methylamino, N-(2-hydroxy-1-phenylethyl)-N-methyl-aminomethyl, N-(2-methoxy-1-phenylethyl)-N-methylamino, N-[2-(acetylamino-phenyl) ethyl]-N-methylamino, N-(furylmethyl)-N-methylamino, N-methyl-N-(thienylmethyl)-amino, N-benzyl-N-(2-hydroxyethyl-aminomethyl, N,N-bis(furylmethyl)-amino, 3,3 -dimethylpiperidinylmethyl, 2-phenylpiperidinyl, 2-phenylpiperidinylmethyl, 3-hydroxy-2-phenylpiperidinylmethyl and 1,2,3,4-tetrahydroisoquinolin-2-yl.

Particular values of R include benzyloxy, N-[1-(fluorophenyl)-2-hydroxyethyl]-amino and N-benzyl-N-methylamino.

Suitable values of $R^a$ include hydrogen, hydroxy and benzyl, especially hydrogen.

Suitably, $R^2$ and $R^3$ independently represent hydrogen or methyl, especially hydrogen.

Suitably, $R^4$ represents hydrogen or methyl, especially hydrogen.

Suitably, $R^5$ and $R^6$ are independently selected from hydrogen, methyl, ethyl, n-propyl, isopropyl, n-butyl, tert-butyl, trifluoromethyl, phenyl, methylphenyl (especially 4-methylphenyl), benzyl and phenethyl.

Suitably, the substituent Z represents hydrogen, fluoro, cyano, hydroxy, methoxy, ethoxy, benzyloxy, methylamino-carbonyloxy, cyano-methoxy, aminocarbonyl-methoxy, methylsulphonyl, aminosulphonyl, N-methylamino-sulphonyl, N,N-dimethylamino-sulphonyl, amino, formylamino, acetylamino, trifluoromethyl-carbonylamino, benzyloxy-carbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylaminocarbonyl or phenethyl-aminocarbonyl; or a group of formula (Za), (Zb), (Zc) or (Zd) as defined above; or an optionally substituted five-membered heteroaromatic ring as specified above.

In a particular embodiment, Z represents —$SO_2NR^5R^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (Zb) in which $R^4$ is hydrogen or methyl. In a subset of this embodiment, X and Y both represent oxygen. In a particular aspect of this subset, the chiral centre denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

A particular sub-class of compounds according to the invention is represented by the compounds of formula IIA, and salts and prodrugs thereof:

(IIA)

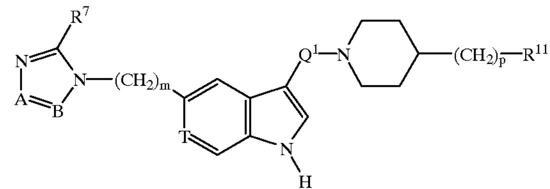

wherein m is zero, 1, 2 or 3, preferably zero or 1;

p is zero, 1 or 2;

$Q^1$ represents a straight or branched alkylene chain containing from 2 to 5 carbon atoms, substituted in any position by one or more fluorine atoms;

T represents nitrogen or CH;

A represents nitrogen or CH;

B represents nitrogen or C—$R^8$;

$R^7$ and $R^8$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;

$R^{11}$ represents —$OR^9$ or —$NR^9R^{10}$; and $R^9$ and $R^{10}$ independently represent hydrogen, $C_{1-6}$ alkyl, $C_{2-6}$ alkenyl, $C_{3-7}$ cycloalkyl($C_{1-6}$)alkyl, indanyl, aryl, aryl($C_{1-6}$)alkyl, heteroaryl or heteroaryl($C_{1-6}$)alkyl, any of which groups may be optionally substituted.

Examples of suitable optional substituents on the groups $R^9$ and $R^{10}$ include $C_{1-6}$ alkyl, halogen, cyano, trifluoromethyl, hydroxy, $C_{1-6}$ alkoxy, aminocarbonyloxy, $C_{2-6}$ alkylcarbonyl, amino, $C_{1-6}$ alkylamino, di($C_{1-6}$)alkylamino, $C_{2-6}$ alkylcarbonylamino, $C_{1-6}$ alkylsulphonylamino and $C_{1-6}$ alkylaminosulphonylmethyl.

Representative values of $R^9$ and $R^{10}$ include hydrogen, methyl, hydroxyethyl, isobutyl, 2,2-dimethylpropyl, allyl, dimethylallyl, 1-cyclohexylethyl, 2-cyclohexylethyl, indanyl, hydroxy-indanyl, phenyl, benzyl, methyl-benzyl, fluorobenzyl, methoxy-benzyl, acetylamino-benzyl, 1-phenylethyl, 2-phenylethyl, 2-hydroxy-1-phenylethyl, 2-methoxy-1-phenylethyl, 2-aminocarbonyloxy-1-phenylethyl, 1-(fluorophenyl)ethyl, 1-(fluorophenyl)-2-hydroxyethyl, 1-(fluorophenyl)-2-methoxyethyl, 1-(acetylamino-phenyl)ethyl, 2-(acetylamino-phenyl)ethyl, 2-hydroxy-1-phenylprop-1-yl, 1-phenylprop-2-yl, 2-phenylprop-2-yl, 1-hydroxy-1 -phenylprop-2-yl, 1-hydroxy-2-phenylprop-2-yl, 1-hydroxy-3-phenylprop-2-yl, furylmethyl, thienylmethyl and pyridylmethyl.

Particular values of $R^9$ and $R^{10}$ include hydrogen, methyl, benzyl and 1-(fluorophenyl)-2-hydroxyethyl.

In relation to formula IIA, the variable p is preferably zero.

Suitably, $Q^1$ represents a straight or branched 3 or 4 carbon alkylene chain, substituted in any position by one or two fluorine atoms. Where the alkylene linkage $Q^1$ is substituted by two fluorine atoms, the gem difluoro substitution pattern is preferred. Particular alkylene chains for $Q^1$ include 2-fluoropropylene, 2,2-difluoropropylene and 2-(fluoromethyl)-propylene.

Particular values of $R^7$ and $R^8$ include hydrogen, methyl, ethyl, benzyl and amino, especially hydrogen.

Another sub-class of compounds according to the invention is represented by the compounds of formula IIB, and salts and prodrugs thereof:

(IIB)

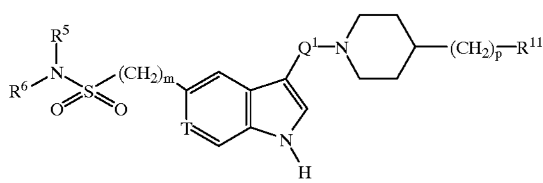

wherein m, p, $Q^1$, T and $R^{11}$ are as defined with reference to formula IIA above; and $R^5$ and $R^6$ are as defined with reference to formula I above.

Particular values of $R^5$ and $R^6$ in relation to formula IIB above include hydrogen and $C_{1-6}$ alkyl, especially hydrogen or methyl. Suitably, one of $R^5$ and $R^6$ represents hydrogen and the other represents hydrogen or methyl.

A further sub-class of compounds according to the invention is represented by the compounds of formula IIC, and salts and prodrugs thereof:

(IIC)

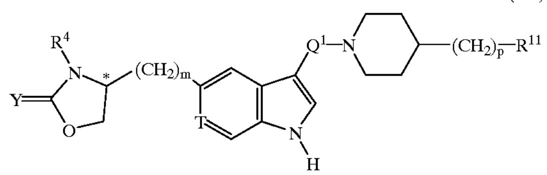

wherein the asterisk * denotes a chiral centre;

m, p, $Q^1$, T and $R^{11}$ are as defined with reference to formula IIA above; and $R^4$ and Y are as defined with reference to formula I above.

Particular values of $R^4$ in relation to formula IIC include hydrogen and methyl.

Preferably, Y in formula IIC is oxygen.

Preferably, the chiral centre denoted by the asterisk * in formula IIC is in the (S) configuration.

In a particular aspect, the present invention provides compounds of formula IIA, IIB and IIC as defined above, and salts and prodrugs thereof, wherein $R^{11}$ represents a group of formula —$NR^9R^{10}$ in which $R^9$ and $R^{10}$ are as defined above.

Specific compounds within the scope of the present invention include:

4-(N-benzyl-N-methylamino)-1-[2-fluoro-3-(5-(1,2,4-triazol-4-yl)-1H-indol-3-yl)propyl]piperidine;

4-[(R)-2-hydroxy-1-(4-fluorophenyl)ethylamino]-1-[2-fluoro-3-(5-(1,2,4-triazol-4-yl)-1H-indol-3-yl)propyl]piperidine;

4-(N-benzyl-N-methylamino)-1-[2,2-difluoro-3-(5-(1,2,4-triazol-4-yl)-1H-indol-3-yl)propyl]piperidine;

4-benzyloxy-1-[2-fluoro-3-(5-(1,2,4-triazol-4-yl)-1H-indol-3-yl)propyl]piperidine;

4-benzyloxy-1-[2,2-difluoro-3-(5-(1,2,4-triazol-4-yl)-1H-indol-3-yl)propyl]piperidine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein T represents CH, U represents C—$R^2$ and V represents N—$R^3$, corresponding to the indole derivatives of formula IC as defined above wherein V represents N—$R^3$, may be prepared by a process which comprises reacting a compound of formula III:

(III)

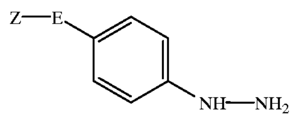

wherein Z and E are as defined above; with a compound of formula IV, or a carbonyl-protected form thereof:

(IV)

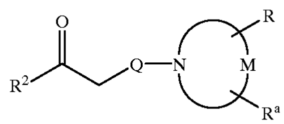

wherein $R^2$, Q, M, R and $R^a$ are as defined above; followed, where required, by N-alkylation by standard methods to introduce the moiety $R^3$.

The reaction between compounds III and IV, which is an example of the well-known Fischer indole synthesis, is suitably carried out by heating the reagents together under mildly acidic conditions, e.g. 4% sulphuric acid at reflux.

Suitable carbonyl-protected forms of the compounds of formula IV include the dimethyl acetal or ketal derivatives.

The Fischer reaction between compounds III and IV may be carried out in a single step, or may proceed via an initial non-cyclising step at a lower temperature to give an intermediate of formula V:

(V)

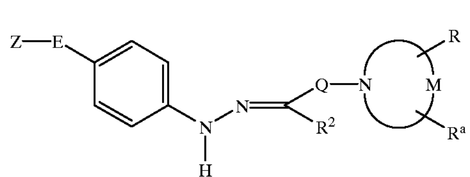

wherein Z, E, Q, $R^2$, M, R and $R^a$ are as defined above; followed by cyclisation using a suitable reagent, e.g. a polyphosphate ester.

The intermediates of formula IV, or carbonyl-protected forms thereof, may be prepared by procedures analogous to those described in the accompanying Examples, or alternatively by reacting a compound of formula VI, or a carbonyl-protected form thereof, with a compound of formula VII:

(VI)

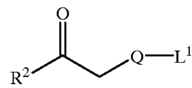

-continued (VII)

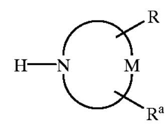

wherein Q, $R^2$, M, R and $R^a$ are as defined above, and $L^1$ represents a suitable leaving group.

The leaving group $L^1$ is suitably a halogen atom, e.g. chlorine or bromine.

Where $L^1$ represents a halogen atom, the reaction between compounds VI and VII is conveniently effected by stirring the reactants under basic conditions in a suitable solvent, for example sodium carbonate or potassium carbonate in 1,2-dimethoxyethane or N,N-dimethyl-formamide, or triethylamine in tetrahydrofuran or acetonitrile, optionally in the presence of sodium iodide.

In an alternative procedure, the compounds according to the invention may be prepared by a process which comprises reacting a compound of formula VII as defined above with a compound of formula VIII:

(VIII)

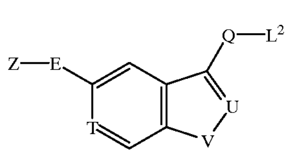

wherein Z, E, Q, T, U and V are as defined above, and $L^2$ represents a suitable leaving group.

The leaving group $L^2$ is suitably an alkylsulphonyloxy or arylsulphonyloxy group, e.g. methanesulphonyloxy (mesyloxy), trifluoromethanesulphonyloxy (triflyloxy) or p-toluenesulphonyloxy (tosyloxy).

Where $L^2$ represents an alkylsulphonyloxy or arylsulphonyloxy group, the reaction between compounds VII and VIII is conveniently carried out in a suitable solvent such as isopropanol, 1,2-dimethoxy-ethane or N,N-dimethylformamide, typically in the presence of a base such as sodium carbonate or potassium carbonate, optionally in the presence of sodium iodide.

The intermediates of formula VIII may be prepared by methods analogous to those described in the accompanying Examples, or by standard procedures well known from the art.

In one representative approach, the compounds of formula VIII wherein T and U both represent CH, V represents NH and $L^2$ represents a mesyloxy or tosyloxy group may be prepared by reacting a compound of formula III as defined above with a compound of formula IX:

(IX)

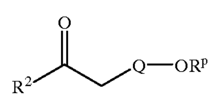

wherein Q and $R^2$ are as defined above, and $R^p$ represents a hydroxy-protecting group such as tert-butyldimethylsilyl; under conditions analogous to those described above for the reaction between compounds III and IV; with removal of the hydroxy-protecting group $R^p$; followed by mesylation or tosylation of the hydroxy-substituted indole derivative thereby obtained using standard procedures, e.g. treatment with mesyl or tosyl chloride in the presence of a base such as triethylamine or pyridine.

In a further procedure, the compounds according to the invention wherein T represents CH, U represents nitrogen and V represents N—$R^3$, corresponding to the indazole derivatives of formula ID as defined above, may be prepared by a process which comprises cyclising a compound of formula X:

(X)

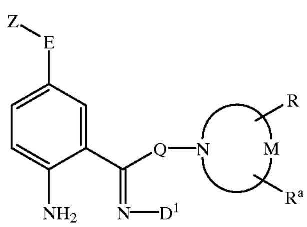

wherein Z, E, Q, M, R and $R^a$ are as defined above, and $D^1$ represents a readily displaceable group; followed, where required, by N-alkylation by standard methods to introduce the moiety $R^3$.

The cyclisation of compound X is conveniently achieved in a suitable organic solvent at an elevated temperature, for example in a mixture of m-xylene and 2,6-lutidine at a temperature in the region of 140° C.

The readily displaceable group $D^1$ in the compounds of formula X suitably represents a $C_{1-4}$ alkanoyloxy group, preferably acetoxy. Where $D^1$ represents acetoxy, the desired compound of formula X may be conveniently prepared by treating a carbonyl compound of formula XI:

(XI)

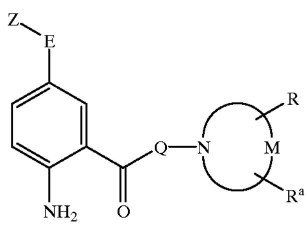

wherein Z, E, Q, M, R and $R^a$ are as defined above; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XI may conveniently be prepared by ozonolysis of the corresponding indole derivative of formula XII:

(XII)

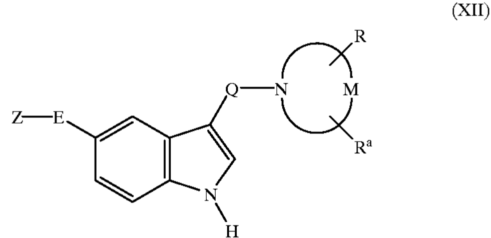

wherein Z, E, Q, M, R and $R^a$ are as defined above; followed by a reductive work-up, advantageously using dimethylsulphide.

The indole derivatives of formula XII may be prepared by methods analogous to those described in the accompanying Examples, or by procedures well known from the art.

In a still further procedure, the compounds according to the invention wherein T represents CH, U represents C—$R^2$ and V represents oxygen or sulphur, corresponding to the benzofuran or benzthiophene derivatives of formula IC wherein V is oxygen or sulphur respectively, may be prepared by a process which comprises cyclising a compound of formula XIII:

(XIII)

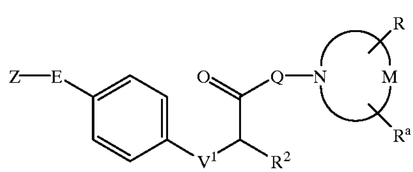

wherein Z, E, Q, $R^2$, M, R and $R^a$ are as defined above, and $V^1$ represents oxygen or sulphur.

The cyclisation of compound XIII is conveniently effected by using polyphosphoric acid or a polyphosphate ester, advantageously at an elevated temperature.

The compounds of formula XIII may be prepared by reacting a compound of formula XIV with a compound of formula XV:

(XIV)

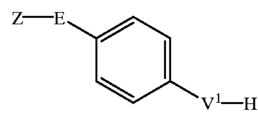

(XV)

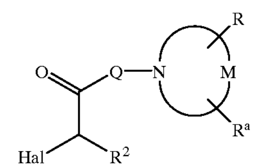

wherein Z, E, Q, $R^2$, $V^1$, M, R and $R^a$ are as defined above, and Hal represents a halogen atom.

The reaction is conveniently effected in the presence of a base such as sodium hydroxide.

The hydroxy and mercapto derivatives of formula XIV may be prepared by a variety of methods which will be readily apparent to those skilled in the art. One such method is described in EP-A-0497512.

In a yet further procedure, the compounds according to the invention may be prepared by a process which comprises reducing a compound of formula XVI:

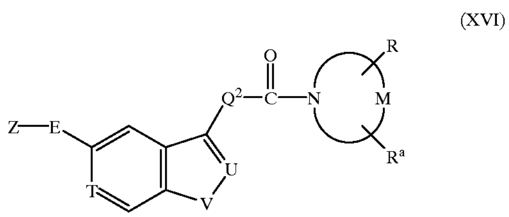

wherein Z, E, T, U, V, M, R and $R^a$ are as defined above, and —$Q^2$—$CH_2$— corresponds to the moiety Q as defined above.

The reaction is suitably carried out by treating the compound of formula XVI with a reducing agent such as lithium aluminium hydride in an appropriate solvent, e.g. diethyl ether, tetrahydrofuran or mixtures thereof.

The compounds of formula XVI above may suitably be prepared by reacting a compound of formula VII as defined above with the appropriate compound of formula XVII:

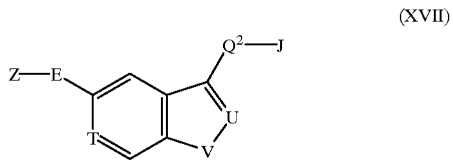

wherein Z, E, T, U, V and $Q^2$ are as defined above, and J represents a reactive carboxylate moiety.

Suitable values for the reactive carboxylate moiety J include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XVII above wherein J is an acid chloride moiety may be prepared by treating the corresponding carboxylic acid derivative with thionyl chloride in toluene. Similarly, the intermediates of formula XVII wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula VII.

The hydrazine derivatives of formula III above may be prepared by methods analogous to those described in WO-A-91/18897, WO-A-94/02477, EP-A-0438230, EP-A-0497512 and EP-A-0548813.

Where they are not commercially available, the starting materials of formula VI, VII, IX, XV and XVII may be prepared by the methods described in the accompanying Examples, or by analogous procedures which will be apparent to those skilled in the art.

It will be understood that any compound of formula I initially obtained from any of the above processes may, where appropriate, subsequently be elaborated into a further compound of formula I by techniques known from the art. For example, a compound of formula I wherein $R^x$ is benzyl initially obtained may be converted into a compound of formula I wherein $R^x$ is hydrogen typically by conventional catalytic hydrogenation, or by transfer hydrogenation using a hydrogenation catalyst such as palladium on charcoal in the presence of a hydrogen donor such as ammonium formate. Moreover, a compound of formula I wherein $R^1$ is hydroxy initially obtained may be converted into the corresponding carbonyl compound (aldehyde or ketone) by treatment with a conventional oxidising agent such as sulphur trioxide-pyridine complex; the resulting carbonyl compound may then be converted in turn into a compound of formula I wherein $R^1$ represents —$NHR^y$, suitably by a standard reductive amination procedure which comprises treating the carbonyl compound with the appropriate amine of formula $R^y$—$NH_2$ in the presence of a suitable reducing agent, typically sodium cyanoborohydride. Alternatively, the carbonyl compound may be converted into a compound of formula I wherein R represents —$CH_2$—$SOR^x$ and $R^a$ represents hydroxy by treatment of the carbonyl compound with the anion of $CH_3$—$SOR^x$. Furthermore, a compound of formula I wherein $R^1$ represents —$NHR^y$ initially obtained may be converted into a further compound of formula I wherein $R^1$ represents —$NR^xR^y$, in which $R^x$ corresponds to the group —$CH_2R^z$, suitably by a reductive amination procedure which comprises treating the compound of formula I wherein $R^1$ represents —$NHR^y$ with the appropriate aldehyde of formula $R^z$—CHO in the presence of a reducing agent such as sodium cyanoborohydride. In addition, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in N,N-dimethylformamide.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry,* ed. J. F. W. McOmie, Plenum Press, 1973; and T. W. Greene & P. G. M. Wuts, *Protective Groups in Organic Synthesis,* John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-$HT_{1D\alpha}$ receptor subtype, inhibit forskolin-stimulated adenylyl cyclase activity, and stimulate [$^{35}$S]-GTPγS binding to membranes from clonal cell lines expressing human cloned receptors.

$5\text{-HT}_{1D\alpha}/5\text{-HT}_{1D\beta}$ Radioligand Binding

Chinese hamster ovary (CHO) clonal cell lines expressing the human $5\text{-HT}_{1D\alpha}$ and $5\text{-HT}_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 $\mu$M) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the $5\text{-HT}_{1D\alpha}$ receptor subtype obtained for the compounds of the accompanying Examples were below 50 nM in each case. Furthermore, the compounds of the accompanying Examples were all found to possess a selective affinity for the $5\text{-HT}_{1D\alpha}$ receptor subtype of at least 10-fold relative to the $5\text{-HT}_{1D\beta}$ subtype.

$5\text{-HT}_{1D\alpha}/5\text{-HT}_{1D\beta}$ Adenylyl Cyclase Assay

Studies were performed essentially as described in *J. Pharmacol. Exp. Ther.,* 1986, 238, 248. CHO clonal cell lines expressing the human cloned $5\text{-HT}_{1D\alpha}$ and $5\text{-HT}_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 $\mu$l aliquot of the membrane suspension was incubated, for 10–15 min, in a final volume of 50 $\mu$l, at 30° C., with or without forskolin (10 $\mu$M), in the presence or absence of test compound. The incubation buffer consisted of 50 mM Tris HCl (pH 7.6 at room temperature), 100 mM NaCl, 30 $\mu$M GTP, 50 $\mu$M cyclic AMP, 1 mM dithiothreitol, 1 mM ATP, 5 mM $MgCl_2$, 1 mM EGTA, 1 mM 3-isobutyl-1-methylxanthine, 3.5 mM creatinine phosphate, 0.2 mg/ml creatine phosphokinase, 0.5–1 $\mu$Ci α-[$^{33}$P]-ATP and 1 nCi [$^3$H]-cyclic AMP. The incubation was initiated by the addition of membrane, following a 5 min preincubation at 30° C., and was terminated by the addition of 100 $\mu$l SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.,* 1974, 58, 541). Functional parameters were determined using a least squares curve fitting programme ALLFIT (*Am. J. Physiol.,* 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the $5\text{-HT}_{1D\alpha}$ receptor obtained for the compounds of the accompanying Examples were below 500 nM in each case. Moreover, the compounds of the accompanying Examples which were tested were all found to possess at least a 10-fold selectivity for the $5\text{-HT}_{1D\alpha}$ receptor subtype relative to the $5\text{-HT}_{1D\beta}$ subtype.

$5\text{-HT}_{1D\alpha}/5\text{-HT}_{1D\beta}$ GTPγS Binding

Studies were performed essentially as described in *Br. J. Pharmacol.,* 1993, 109, 1120. CHO clonal cell lines expressing the human cloned $5\text{-HT}_{1D\alpha}$ and $5\text{-HT}_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, $MgCl_2$ 10, pargyline 0.01; ascorbate 0.1%; pH 7.4 at room temperature) at a concentration of 40 $\mu$g protein/ml for the $5\text{-HT}_{1D\alpha}$ receptor transfected cells and 40–50 $\mu$g protein/ml for the $5\text{-HT}_{1D\beta}$ receptor transfected cells. The membrane suspension was then incubated, in a volume of 1 ml, with GDP (100 $\mu$M for $5\text{-HT}_{1D\alpha}$ receptor transfected cells, 30 $\mu$M for the $5\text{-HT}_{1D\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the $5\text{-HT}_{1D\alpha}$ receptor obtained for the compounds of the accompanying Examples were below 500 nM in each case. Moreover, the compounds of the accompanying Examples which were tested were all found to possess at least a 10-fold selectivity for the $5\text{-HT}_{1D\alpha}$ receptor subtype relative to the $5\text{-HT}_{1D\beta}$ subtype.

INTERMEDIATE 1

4-(1,2,4-Triazol-4-yl)phenylhydrazine

Prepared as described in WO 94/03446.

INTERMEDIATE 2

(R,S)-2-Fluoro-3-[5-(1,2,4-triazol-4-yl)-1H-indol-3-yl]propan-1-ol a) (R,S)-2-Fluoro-5-hexen-1-ol To a cooled (−10° C.) and stirred mixture of hydrogen fluoride-pyridine (70% HF; 10 ml) and anhydrous dichloromethane (60 ml), in a polypropylene tube, was added dropwise via syringe neat 1,2-epoxy-5-hexene (13.8 ml) over 20 minutes, under nitrogen. After a further 20 minutes, the yellow solution was carefully poured into ice-water-concentrated ammonia (57 ml of ammonia; total volume 400 ml) and the aqueous mixture was saturated with solid sodium chloride. Products were extracted with diethyl ether (2×500 ml) and the combined ethereal solutions were washed with brine (45 ml), brine—10% aqueous sodium bicarbonate (5:1, 60 ml), then dried ($MgSO_4$) and concentrated (bath temperature 30° C.). Flash chromatography of the residual liquid (silica gel, hexane-diethyl ether, 65:35), followed by purification on alumina (activity III, dichloromethane), gave 4.4 g of the title compound as a colourless liquid; $\delta_H$ (360 MHz, $CDCl_3$) 1.56–1.90 (2H, m), 2.10–2.30 (2H, m), 3.62–3.80 (2H, m), 4.48–4.70 (1H, dm, J=50 Hz), 5.00–5.12 (2H, m), 5.75–5.88 (1H, m).

b) (R,S)-6-tert-Butyldimethylsilyloxy-5-fluoro-1-hexene

To a stirred solution of 2-fluoro-5-hexen-1-ol (4.4 g, 37.2 mmol) in anhydrous dimethylformamide (125 ml) were added imidazole (7.60 g, 111.7 mmol) and tert-butyldimethylsilyl chloride (8.42 g, 55.9 mmol), under nitrogen. After being stirred at room temperature for 7.5 hours, the mixture was diluted with diethyl ether (400 ml) and it was washed with water (150 ml), 1M hydrochloric acid (100 ml), 5% aqueous sodium bicarbonate (100 ml), brine (100 ml), then dried ($MgSO_4$) and concentrated. Flash chromatography of the residue (silica gel, petrol ether (40–60) to petrol ether (40–60)—5% diethyl ether) gave the title compound as a colourless liquid. Some impure fractions were repurified on alumina (activity III; petroleum ether (40–60)); total yield of product 6.72 g (77.7%); $\delta_H$ (360 MHz, $CDCl_3$) 0.07 (6H, s), 0.90 (9H, s), 1.58–1.84 (2H, m), 2.10–2.30 (2H, m), 3.71 (2H, dd, J=22.2 and 4.7 Hz), 4.40–4.60 (1H, dm, J=49 Hz), 4.96–5.10 (2H, m), 5.75–5.88 (1H, m).

c) (R,S)-5-tert-Butyldimethylsilyloxy-4-fluoropentanal

Ozone was bubbled through a cooled (−75° C.) and stirred solution of the preceding olefin (6.7 g, 28.8 mmol) in anhydrous dichloromethane (150 ml) until a blue colour persisted (45 minutes). Oxygen was then bubbled for 10 minutes through the solution before it was kept under a nitrogen atmosphere. Anhydrous dimethyl sulfide (10 ml, 136.2 mmol) was added at −78° C. and the mixture was allowed to warm to room temperature. After 2 hours, solvents were removed under vacuum (bath temperature 32° C.) and the residue was purified by flash chromatography (silica gel, hexane-diethyl ether, 80:20) to give 5.45 g of the intermediate ozonide and 1 g of the required title product, as pale pink liquids. The ozonide (5.4 g, 19.28 mmol) in anhydrous dichloromethane (125 ml) was cooled to −78° C., under nitrogen, and anhydrous triethylamine (5.4 ml, 38.6 mmol) was added over 2 minutes. The resulting solution was allowed to warm to room temperature and stirred for 2.5 hours. The mixture was half concentrated under vacuum and directly chromatographed on silica gel (dichloromethane) to give 3.60 g of the title compound as a colourless liquid; $\delta_H$ (360 MHz, $CDCl_3$) 0.07 (6H, s), 0.90 (9H, s), 1.90–2.05 (2H, m), 2.54–2.72 (2H, m), 3.73 (2H, dd, J=21.3 and 4.5 Hz), 4.40–4.62 (1H, (dm, J=49.5 Hz), 9.81 (1H, dd, J=2.1 and 0.9 Hz).

d) (R,S)-2-Fluoro-3-[5-(1,2,4-triazol-4-yl)-1H-indol-3-yl] propan-1-ol

To a stirred solution of the preceding aldehyde (4.60 g, 19.6 mmol) in dioxane (170 ml) was added 4-(1,2,4-triazol-4-yl)phenylhydrazine (3.80 g, 21.1 mmol) followed by water (20 ml). After 15 minutes, 2M hydrochloric acid (11 ml) was added and the mixture was refluxed for 68 hours under nitrogen. Solvents were removed under vacuum and the residue was purified by flash chromatography (silica gel, dichloromethane-methanol, 90:10), then alumina (activity III, dichloromethane-methanol-ammonia, 95:5:0.5; then dichloromethane-methanol-ammonia, 90:10:1), to give 700 mg of the title compound as a yellow solid; $\delta_H$ (360 MHz, DMSO-$_6$) 2.98–3.10 (2H, m), 3.44–3.66 (2H, m), 4.66–4.88 (1H, dm, J=49 Hz), 4.93 (1H, t, J=5.6 Hz), 7.32 (1H, dd, J=8.5 and 1.9 Hz), 7.35 (1H, d, J=2.1 Hz), 7.50 (1H, d, J=8.5 Hz), 7.82 (1H, d, J=1.9 Hz), 9.00 (2H, s), 11.19 (1H, s); m/e (ES) 261 ($M^+$+1).

EXAMPLE 1

4-(N-Benzyl-N-methylamino)-1-{(R,S)-2-fluoro-3-[5-(1,2,4-triazol-4-yl)-1H-indol-3-yl]propyl}piperidine. 2.25 Hydrogen Oxalate. 1.0 Hydrate a) 1-tert-Butyloxycarbonyl-4-N-benzyl-N-methylamino) piperidine To a stirred solution of 1-tert-butyloxycarbonyl-4-piperidone (3.30 g, 16.5 mmol) and benzylamine (1.64 ml, 15.0 mmol) in a mixture of methanol (150 ml) and glacial acetic acid (3.4 ml, 60 mmol) was added sodium cyanoborohydride (1.04 g, 16.5 mmol), and the resulting mixture was stirred at room temperature for 2 hours 15 minutes. A solution of formaldehyde (38% w/v aqueous solution; 1.42 ml) in methanol (5 ml) was added and stirring was continued for 16 hours. 4N Sodium hydroxide (35 ml) was added and the methanol was removed under vacuum. The residue was diluted with water (50 ml) and products were extracted with diethyl ether (2×300 ml). The combined organic phases were washed with brine (50 ml), dried ($Na_2SO_4$) and concentrated. Flash chromatography of the residue (silica gel, dichloromethane-methanol-ammonia, 97:3:0.2) followed by repurification of impure fractions on alumina (activity III, dichloromethane) afforded 3.98 g (87.4%) of the title compound as a colourless thick oil; $\delta_H$ (360 MHz, $CDCl_3$) 1.46 (9H, s), 1.44–1.56 (2H, m), 1.76–1.85 (2H, m), 2.20 (3H, s), 2.52–2.76 (3H, m), 3.57 (2H, s), 4.10–4.22 (2H, m), 7.20–7.36 (5H, m); m/e (ES) 305 ($M^+$+1).

b) 4-(N-Benzyl-N-methylamino)piperidine

A solution of the preceding piperidine (3.95 g, 12.97 mmol) in a mixture of dichloromethane (40 ml) and trifluoroacetic acid (40 ml) was allowed to stand at room temperature for 3 hours. Solvents were removed under vacuum and the residue azeotroped with toluene-methanol (5:1, 100 ml). The remaining residue was dissolved in 4N sodium hydroxide (50 ml) and extracted with dichloromethane (2×50 ml). The combined organic solutions were washed with brine (50 ml), dried ($Na_2SO_4$) and concentrated to give the title compound (2.70 g, 100%) which was used in the next step without further purification; $\delta_H$ (360 MHz, $CDCl_3$) 1.52 (2H, dq, J=12.2 and 4.0 Hz), 1.80–1.90 (2H, m), 2.21 (3H, s), 2.50–2.66 (3H, m), 3.12–3.22 (2H, m), 3.58 (2H, s), 7.18–7.36 (5H, m); m/e (ES) 205 ($M^+$+1).

c) 4-(N-Benzyl-N-methylamino)-1-{(R,S)-2-fluoro-3-[5-(1,2,4-triazol-4-yl)-1H-indol-3-yl]propyl}piperidine. 2.25 Hydrogen Oxalate. 1.0 Hydrate To a stirred suspension of Intermediate 2 (200 mg, 0.77 mmol) in anhydrous tetrahydrofuran (30 ml) was added anhydrous triethylamine (214 μl, 1.54 mmol) followed by methanesulphonyl chloride (121 μl, 1.54 mmol). After being stirred at room temperature for 2 hours 10 minutes, under nitrogen, the mixture was diluted with ethyl acetate (125 ml), washed with brine-water (1:1, 25 ml), brine (25 ml), then dried ($MgSO_4$) and concentrated.

A mixture of the mesylate thus obtained, anhydrous potassium carbonate (128 mg) and 4-(N-benzyl-N-methylamino)piperidine (800 mg) in isopropanol (35 ml) was refluxed, under nitrogen, for 65 hours. Solvents were removed under vacuum, the residue was dissolved in water (40 ml) and products were extracted with ethyl acetate (2×100 ml). The combined organic solutions were washed with brine (1×40 ml), dried ($Na_2SO_4$) and concentrated. Flash chromatography of the residue (silica gel, dichloromethane-methanol-ammonia, 95:5:0.5) followed by purification on alumina (activity III, dichloromethane-methanol-ammonia, 97:3:0.2), and finally flash chromatography (silica gel, dichloromethane-methanol, 80:20) gave 188 mg (54.8%) of the title compound free base. The oxalate salt was prepared from ethanol-diethyl ether, mp 110–117° C. (Found: C, 54.81; H, 5.75; N, 12.55. $C_{26}H_{31}FN_6$×2.25$C_2H_2O_4$×1.0$H_2O$ requires: C, 54.91; H, 5.67; N, 12.60%). $\delta_H$ (360 MHz, $D_2O$) 2.08–2.24 (2H, m), 2.36–2.48 (2H, m), 2.75 (3H, s), 3.10–3.34 (4H, m), 3.38–3.58 (2H, m), 3.62–3.92 (3H, m), 4.28–4.50 (2H, m), 5.26–5.48 (1H, m), 7.32 (1H, d, J=8.7 Hz), 7.40–7.55 (6H, m), 7.62 (1H, d, J=8.7 Hz), 7.77 (1H, s), 8.92 (2H, s); m/e (ES) 447 $M^+$+1).

EXAMPLE 2

1-{(R,S)-2-Fluoro-3-[5-(1,2,4-triazol-4-yl)-1H-indol-3-yl]propyl}-4-{[(R)-2-hydroxy-1-(4-fluorophenyl)ethyl]amino}piperidine. 2.0 Hydrogen Oxalate. 1.2 Hydrate.

a) (R)-2-Amino-2-(4-fluorophenyl)ethanol

To a stirred 1.0M solution of lithium aluminium hydride in THF (23.5 ml, 23.5 mmol), cooled to 0° C. under Ar, was added portionwise over 1 h 45 min solid (−)-4-fluoro-D-α-phenylglycine (1.98 g, 11.7 mmol). The reaction mixture was then stirred at room temperature overnight before carefully adding water (0.89 ml), then 4N NaOH solution (0.89 ml) and then water (2.68 ml). The mixture was stirred for a few minutes, then filtered, and the filtrate was evaporated in vacuo. Flash chromatography of the residue (silica gel, dichloromethane-methanol-ammonia, 90:10:1) gave 1.499 g (82%) of the title compound as a white solid; $\delta_H$ (250 MHz, $CDCl_3$) 3.52 (1H, dd, J=10.7 and 8.2 Hz), 3.71 (1H, dd, J=10.7 and 4.4 Hz), 4.06 (1H, dd, J=8.1 and 4.4 Hz), 6.99–7.08 (2H, m), 7.28–7.34 (2H, m).

b) 1-tert-Butyloxycarbonyl-4-{[(R)-2-hydroxy-1-(4-fluorophenyl)ethyl]amino}piperidine To a stirred solution of 1-tert-butyloxycarbonyl-4-piperidone (3.30 g, 16.5 mmol) and (R)-2-amino-2-(4-fluorophenyl)ethanol (2.33 g, 15.0 mmol) in a mixture of methanol (150 ml) and glacial acetic acid (3.4 ml, 60 mmol) was added sodium cyanoborohydride (1.04 g, 16.6 mmol), and the resulting mixture was stirred at room temperature for 18.5 hours. 4N Sodium hydroxide (30 ml) was added and the methanol was removed under vacuum. The remaining residue was diluted with water (50 ml) and products were extracted with diethyl ether (2×300 ml). The combined ethereal phases were washed with brine (50 ml), dried ($Na_2SO_4$) and concentrated. Flash chromatography of the residue (silica gel, dichloromethane-methanol-ammonia, 95:5:0.5) gave 4.60 g (90.7%) of the title compound as a thick oil which solidified on standing; $\delta_H$ (360 MHz, $CDCl_3$) 1.16–1.30 (2H, m), 1.44 (9H, s), 1.58–1.68 (1H, m), 1.84–1.92 (1H, m), 2.48–2.58 (1H, m), 2.66–2.78 (2H, m), 3.45 (1H, dd, J=10.7 and 8.7 Hz), 3.65 (1H, dd, J=10.7 and 4.5 Hz), 3.90–4.04 (3H, m), 7.00–7.08 (2H, m), 7.22–7.30 (2H, m); m/e (ES) 339 ($M^+$+1).

c) 4-{[(R)-2-Hydroxy-1-(4-fluorophenyl)ethyl]amino}piperidine

The title compound was prepared form the product of the preceding step using a similar method to that described for Example 1, Step b. $\delta_H$ (360 MHz, $CDCl_3$+DMSO-$d_6$) 0.90–1.04 (2H, m), 1.38–1.48 (1H, m), 1.68–1.78 (1H, m), 2.12–2.32 (3H, m), 2.72–2.85 (2H, m), 3.23 (1H, dd, J=10.6 and 8.6 Hz), 3.40 (1H, dd, J=10.6 and 4.2 Hz), 3.75 (1H, dd, J=8.6 and 4.2 Hz), 6.74–6.82 (2H, m), 7.17–7.45 (2H, m); m/e (ES) 239 ($M^+$+1).

d) 1-{(R,S)-2-Fluoro-3-[5-(1,2,4-triazol-4-yl)-1H-indol-3-yl]propyl}-4-{[(R)-2-hydroxy-1-(4-fluorophenyl)ethyl]amino}piperidine. 2.0 Hydrozen Oxalate. 1.2 Hydrate The title compound free base was prepared from the product of the preceding step and Intermediate 2, following a similar procedure to that described for Example 1, step c. The oxalate salt was prepared from ethanol-diethyl ether, mp 130–140° C. (Found: C, 52.77; H, 5.60; N, 12.31. $C_{26}H_{30}F_2N_6O$×2.0$C_2H_2O_4$×1.2$H_2O$ requires: C, 52.82; H, 5.38; N, 12.32%). $\delta_H$ (360 MHz, DMSO-$d_6$) 1.56–1.78 (2H, m), 1.86–2.04 (2H, m), 2.08–2.32 (2H, m), 2.64–2.82 (3H, m), 2.96–3.10 (4H, m), 3.71 (2H, d, J=5.6 Hz), 4.36 (1H, m), 4.96–5.18 (1H, m), 7.22–7.36 (4H, m), 7.50 (1H, d, J=8.6 Hz), 7.56–7.60 (2H, m), 7.80 (1H, s), 9.00 (2H, s), 11.26 (1H, s); m/e (ES) 481 ($M^+$+1).

EXAMPLE 3

4-(N-Benzyl-N-methylamino)-1-{2,2-difluoro-3-[5-(1,2,4-triazol-4-yl)-1H-indol-3-yl]propyl}piperidine a) A solution of hexamethylene tetramine (12 g) and 5-(1,2,4-triazol-4-yl)-1H-indole (10.5 g, 57.1 mmol) in acetic acid (125 ml, 30% v/v) were heated at reflux for 3 hours. The reaction was neutralized with potassium carbonate and the water removed in vacuo. The residue was triturated with water and the solid collected to give 5-(1,2,4-triazol-4-yl)-3-(carboxaldehyde)-1H-indole as a brown solid. m/e (ES) 213 ($M^+$+1).

b) A suspension of the product from above (1.01 g, 4.8 mmol), N,N-dimethylaminopyridine (DMAP) (47 mg) and di-tert-butyldicarbonate (1.03 g), in 25 ml dichloromethane, was stirred for 8 hours. Further quantities of DMAP (50 mg) and di-tert-butyldicarbonate (200 mg) were added after 1.5 hours. The reaction was concentrated, and the solid triturated with methanol, to give 5-(1,2,4-triazol-4-yl)-3-(carboxaldehyde)-1-(tert-butoxycarbonyl)indole as a beige solid. $\delta_H$ (250 MHz, $d_6$-DMSO) 1.90 (9H, s), 7.96–8.00 (1H, m), 8.46 (1H, d, J=10 Hz), 8.54 (1H, d, J=3 Hz), 9.03 (1H, s), 9.38 (2H, s), 10.34 (1H, s). m/e (ES) 313 ($M^+$+1).

c) A suspension of activated zinc dust (85 mg) and the aldehyde from above (312 mg, 1 mmol) in 3 ml THF and 5 drops DMF was heated to reflux under a nitrogen atmosphere. Ethyl bromodifluoroacetate (0.14 ml, 1.1 mmol) was added. After 15 minutes, a further 0.5 eq of ethyl bromodifluoroacetate was added, followed after 15 minutes by phenyl chlorothionoformate (0.18 ml, 1.3 mmol). The reaction was heated at reflux 1.5 hours, and partitioned between water-ethyl acetate. The combined organic phases were separated, dried ($MgSO_4$), concentrated and chromatographed using 5% methanol-dichloromethane. The partially purified product was heated to reflux in 15 ml degassed toluene with tributyl tin hydride (0.27 ml, 1 mmol) and α,α'-azobisisobutyronitrile (118 mg). After 2.5 hours, the reaction was concentrated, and chromatographed using 2→5% methanol-dichloromethane. Ethyl 2,2-difluoro-3-[5-(1,2,4-triazol-4-yl)-1-tert-butoxycarbonylindol-3-yl]propanoate was obtained as a yellow oil. m/e (ES) 421 ($M^+$+1). $\delta_H$ (250 MHz, $CDCl_3$) 0.92 (3H, t, J=7.5 Hz), 1.69 (9H, s), 3.49 (2H, t, J=15 Hz), 4.28 (2H, q, J=7.5 Hz), 7.30–7.35 (1H, m), 7.56 (1H, m), 7.67 (1H, s), 8.30–8.34 (1H, m), 8.50 (2H, s).

d) A solution of the product from above (179 mg, 0.4 mmol) in 3 ml ethanol was treated with sodium borohydride (20 mg) and the reaction monitored. When all the starting material had reacted, the reaction was quenched by addition of water. The ethanol was removed in vacuo, and the product extracted with ethyl acetate. The organic phase was dried ($MgSO_4$), concentrated and chromatographed using 5% methanol-dichloromethane as eluent. 2,2-Difluoro-3-[5-(1,2,4-triazol-4-yl)-1-tert-butoxycarbonylindol-3-yl]propan-1-ol was obtained as a yellow oil. m/e (ES) 379 ($M^+$+1). $\delta_H$ (250 MHz, $CDCl_3$) 1.69 (9H, s), 3.42 (2H, t, J=17.5 Hz), 3.77 (2H, t, J=12.5 Hz), 7.30–7.34 (1H, m), 7.69 (1H, s), 7.74 (1H, s), 8.29–8.32 (1H, m), 8.60 (2H, br s).

e) A solution of the product from above (80 mg, 0.21 mmol) in 10 ml anhydrous dichloromethane and pyridine (70 μl) was cooled to an internal temperature of −50° C. under a nitrogen atmosphere. Trifluoromethanesulfonic anhydride (71 μl) was added, and the reaction allowed to stir at −25→−50° C. for 1.5 h. Five ml of water was added, and the reaction allowed to attain room temperature. The organic phase was separated, dried ($MgSO_4$), and concentrated. The crude triflate was dissolved in 3 ml anhydrous DMF and heated 120° C. for 10 minutes with potassium carbonate (58 mg) and the amine from Example 1, step b (86 mg). The reaction was partitioned between ethyl acetate and water. The organic phase was separated, dried ($MgSO_4$) and concentrated, then deprotected as described in Example 1, step b.

The title compound free base was obtained by chromatography using 3% methanol-dichloromethane→methanol-dichloromethane-ammonia (5:94:1). The salt was prepared as described in Example 1, step c. mp. softens at 85° C. $\delta_H$ (360 MHz, $d_6$-DMSO) 1.66–1.80 (2H, m), 1.90–2.00 (2H, m), 2.16–2.24 (2H, m), 2.54 (3H, s), 2.70 (2H, t, J=14.4 Hz), 2.90–3.00 (2H, m), 3.06–3.20 (1H, m), 3.44 (2H, t, J=14.4 Hz), 4.20–4.28 (2H, m), 7.32–7.60 (8H, m), 7.84 (1H, s), 9.0 (2H, s), 11.4 (1H, s). m/e (ES) 465 ($M^+$+1).

EXAMPLE 4

4-Benzyloxy-1-{(R,S)-2-fluoro-3-[5-(1,2,4-triazol-4-yl)-1H-indol-3-yl]propyl}piperidine Hydrogen Oxalate 4-Benzyloxypiperidine (0.88 g, 4.62 mmol) (Example 5, step b) was reacted as described in Example 1, step c to give the title compound, mp. softens at 130° C. (Found: C, 60.13; H, 5.87; N, 12.42. $C_{25}H_{28}FNSO$. $C_2H_2O_4$ requires C, 61.94; H, 5.76; N, 13.38). $\delta_H$ (360 MHz, $d_6$-DMSO) 1.60–1.80 (2H, m), 1.80–2.00 (2H, m), 2.54–2.70 (2H, m), 2.80–3.20 (6H, m), 3.46–3.78 (1H, m), 4.50 (2H, s), 5.00–5.24 (1H, m), 7.20–7.40 (7H, m), 7.46–7.56 (1H, m), 7.78 (1H, s), 8.87 (2H, s), 11.04 (1H, s). m/e (ES) 434 ($M^+$+1).

EXAMPLE 5

4-Benzyloxy-1-{2,2-difluoro-3-[5-(1,2,4-triazol-4-yl)-1H-indol-3-yl]propyl}piperidine a) A solution of N-tert-butoxycarbonylpiperidin-4-ol (25 g, 0.124 mol) in 100 ml anhydrous THF was added to a suspension of sodium hydride (5.96 g, 0.15 mol, pentane washed) in 100 ml anhydrous THF at 0° C. The reaction was stirred at 0° C. for 1 hour, then treated with a solution of benzyl bromide (25.65 g, 0.15 mol) in 20 ml anhydrous THF. The reaction was allowed to stand for 20 h at room temperature, cooled to 0° C., and 50 ml water was added cautiously. The product was extracted using ethyl acetate, the combined organic extracts were washed with water, dried ($MgSO_4$) and concentrated. Chromatography using petroleum ether→20% ethyl acetate-petroleum ether gave 4-benzyloxy-1-tert-butoxycarbonyl-piperidine as a colourless solid. $\delta_H$ (250 MHz, $CDCl_3$) 1.45 (9H, s), 1.51–1.65 (2H, m), 1.80–1.94 (2H, m), 3.04–3.15 (2H, m), 3.51–3.61 (1H, m), 3.70–3.84 (2H, m), 4.56 (2H, m), 7.26–7.35 (5H, m). m/e (ES) 292.

b) The product from above (6.1 g, 21 mmol) was reacted as described in Example 1, step b to give 4-benzyloxypiperidine as a crystalline solid. $\delta_H$ (360 MHz, $CDCl_3$) 1.43–1.57 (2H, m), 1.91–2.09 (2H, m), 2.55–2.66 (2H, m), 3.06–3.15 (2H, m), 3.41–3.52 (1H, m), 4.56 (2H, s), 7.12–7.37 (5H, m). m/e (ES) 192 ($M^+$+1).

c) Ethyl bromodifluoroacetate (32.07 g, 0.158 mol) and 4-benzyloxy-piperidine (27.36 g) were stirred at room temperature in ethanol overnight. Ethanol and excess reagents were removed in vacuo and the residue was chromatographed using 10% ethyl acetate-petroleum ether as eluent to give 1-(2-bromo-2,2-difluoroacetamido)-4-benzyloxypiperidine. $\delta_H$ (250 MHz, $CDCl_3$) 1.54–1.92 (4H, m), 3.60–3.87 (5H, m), 4.56 (2H, s), 7.25–7.38 (5H, m).

d) A solution of allyltributyl tin (17.7 ml) and the product from above (19.9 g, 0.057 mol) in 200 ml of degassed toluene was heated to reflux under a nitrogen atmosphere in the presence of α,α'-azobisisobutyronitrile (0.5 g) for 48 h. Further aliquots of AIBN were added, and refluxing was continued until the reaction had gone to completion. The reaction was concentrated and chromatographed using 5% ethyl acetate-petroleum ether to give 1-(2,2-difluoro-4-pentenamido)-4-benzyloxypiperidine. $\delta_H$ (360 MHz, $CDCl_3$) 1.72–1.76 (2H, m), 1.86–1.91 (2H, m), 2.85–2.97 (2H, dt, J=18 and 7.2 Hz), 3.44–3.60 (2H, m), 3.67–3.71 (1H, m), 3.80–3.96 (2H, m), 4.56 (2H, s), 5.23 (1H, s), 5.26 (1H, d, J=7.2 Hz), 5.81–5.92 (1H, m), 7.25–7.35 (5H, m). m/s (ES) 310 ($M^+$+1).

e) A solution of the product from above (7.0 g, 0.023 mol) in 20 ml anhydrous THF was treated with 9-BBN (182 ml of 0.5M solution) and was heated to reflux for 8 h. The reaction was cooled, and carefully basified to pH11–12 using 4N NaOH. Hydrogen peroxide (30% w/v solution, 7.82 g, 26 ml) was added slowly to the cooled reaction. The reaction was allowed to stand for 18 h, adjusted to pH8–9, poured into water, and extracted with diethyl ether. The organic extracts were washed with brine, water, dried ($MgSO_4$) and concentrated in vacuo. Purification by chromatography using 10% ethyl acetate petroleum ether as eluent gave 1-(2,2-difluoro-5-hydroxypentan-1-yl)-4-benzyloxypiperidine as a pale yellow oil. $\delta_H$ (250 MHz, $CDCl_3$) 1.60–2.20 (8H, m), 1.36–2.54 (2H, m), 2.70 (2H, t, J=15 Hz), 2.84–3.00 (2H, m), 3.40–3.54 (1H, m), 3.68 (2H, t, J=5 Hz), 4.53 (2H, s), 7.26–7.35 (5H, m). m/s (ES) 314 ($M^+$+1).

f) A solution of the product from above (3.3 g) in 20 ml anhydrous dimethylsulphoxide was stirred with triethylamine (10.35 ml) at 0° C. under a nitrogen atmosphere. Sulphur trioxide-pyridine (2.51 g) was added in portions. The reaction was stirred at room temperature for 1½ hours, a further portion of $SO_3$-pyridine (0.2 g) added, and stirring continued for 45 minutes. Water was added carefully, the product extracted into ethyl acetate, the organic phase washed with brine, dried ($MgSO_4$), concentrated and purified by dry flash column chromatography using 10% ethyl acetate-petroleum ether as eluent. 1-(2,2-Difluoro-5-pentanal)-4-benzyloxypiperidine was obtained as a pale yellow oil. $\delta_H$ (250 MHz, $CDCl_3$) 1.60–1.80 (2H, m), 1.84–2.00 (2H, m), 2.20–2.46 (6H, m), 2.64–2.94 (4H, m), 3.44 (br s, 1H), 4.53 (2H, s), 7.24–7.38 (5H, s), 9.90 (br s, 1H). m/e (ES) 312 ($M^+$+1).

g) The product from above was reacted in a similar manner as described for Intermediate 2 step d, using 4% sulfuric acid instead of dioxane-water, to give the title compound free base. mp. 169.5–170.3° C. (ethanol). (Found: C, 66.14; H, 6.09; N, 15.31. $C_{25}H_{27}F_2N_5O$ requires C, 66.50; H, 6.05; N, 15.51). $\delta_H$ (360 MHz, $d_6$-DMSO) 1.49–1.52 (2H, m), 1.80–1.90 (2H, m), 2.22–2.32 (2H, m), 2.60–2.78 (4H, m), 3.31–3.45 (3H, m), 7.26–7.38 (7H, m), 7.50–7.52 (1H, m), 7.81 (1H, s), 8.98 (2H, s), 11.32 (1H, s). m/e (ES) 452 ($M^+$+1).

We claim:

1. A compound of formula I, or a salt or prodrug thereof:

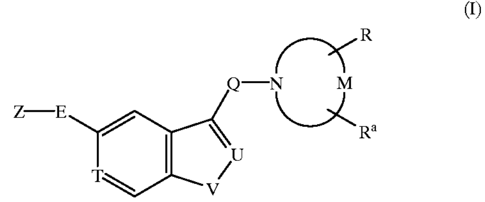

wherein

Z represents hydrogen, halogen, cyano, nitro, trifluoromethyl, $—OR^5$, $—OCOR^5$, $—OCONR^5R^6$, $—OCH_2CN$, $—OCH_2CONR^5R^6$, $—SR^5$, $—SOR^5$, $—SO_2R^5$, $—SO_2NR^5R^6$, $—NR^5R^6$, $—NR^5COR^6$, $—NR^5CO_2R^6$, $—NR^5SO_2R^6$, $—COR^5$, $—CO_2R^5$, $—CONR^5R^6$, or a group of formula (Za), (Zb), (Zc) or (Zd):

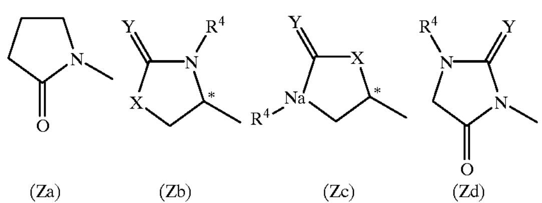

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, substituted in any position by one or more fluorine atoms;

T represents CH;

U represents C—$R^2$;

V represents N—$R^3$;

$R^2$, $R^3$ and $R^4$ independently represent hydrogen or $C_{1-6}$ alkyl;

$R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring;

M represents the residue of a piperidine ring;

R represents a group of formula —W—$R^1$;

W represents a chemical bond or a straight or branched alkylene chain containing from 1 to 4 carbon atoms, optionally substituted in any position by a hydroxy group;

$R^1$ represents —$OR^x$, —$SR^x$, —$SOR^x$, —$SO_2R^x$ or —$NR^xR^y$;

$R^x$ and $R^y$ independently represent hydrogen, hydrocarbon or a heterocyclic group; or $R^x$ and $R^y$ together represent a $C_{2-6}$ alkylene group, which alkylene group may be optionally substituted by one or more substituents selected from $C_{1-6}$ alkyl, aryl and hydroxy, or fused with a phenyl ring; and $R^a$ represents hydrogen, hydroxy, hydrocarbon or a heterocyclic group.

2. A compound as claimed in claim 1 represented by formula IIA, and salts and prodrugs thereof:

(IIA)

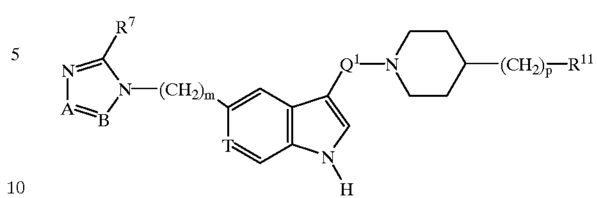

wherein m is zero, 1, 2 or 3;

p is zero, 1 or 2;

$Q^1$ represents a straight or branched alkylene chain containing from 2 to 5 carbon atoms, substituted in any position by one or more fluorine atoms;

T represents CH;

A represents nitrogen or CH;

B represents nitrogen or C—$R^8$;

$R^7$ and $R^8$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;

$R^{11}$ represents —$OR^9$ or —$NR^9R^{10}$; and $R^9$ and $R^{10}$ independently represent hydrogen, $C_{1-6}$ alkyl, $C_{2-6}$ alkenyl, $C_{3-7}$ cycloalkyl($C_{1-6}$)alkyl, indanyl, aryl, aryl($C_{1-6}$)alkyl, heteroaryl or heteroaryl($C_{1-6}$)alkyl, any of which groups may be optionally substituted.

3. A compound as claimed in claim 1 represented by formula IIB, and salts and prodrugs thereof:

(IIB)

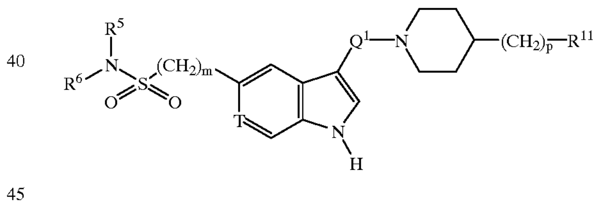

wherein m, p, $Q^1$, T and $R^{11}$ are as defined in claim 2; and $R^5$ and $R^6$ are as defined in claim 1.

4. A compound as claimed in claim 1 represented by formula IIC, and salts and prodrugs thereof:

(IIC)

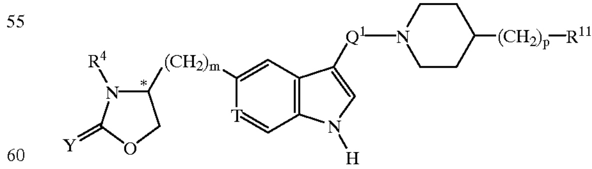

wherein the asterisk * denotes a chiral centre;

m, p, $Q^1$, T and $R^{11}$ are as defined in claim 2; and $R^4$ and Y are as defined in claim 1.

5. A compound as claimed in claim 2 wherein $R^{11}$ represents a group of formula —$NR^9R^{10}$.

6. A compound selected from:

4-(N-benzyl-N-methylamino)-1-[2-fluoro-3-(5-(1,2,4-triazol-4-yl)-1H-indol-3-yl)propyl]piperidine;

4-[(R)-2-hydroxy-1-(4-fluorophenyl)ethylamino]-1-[2-fluoro-3-(5-(1,2,4-triazol-4-yl)-1H-indol-3-yl)propyl]piperidine;

and salts and prodrugs thereof.

7. A compound selected from:

4-(N-benzyl-N-methylamino)-1-[2,2-difluoro-3-(5-(1,2,4-triazol-4-yl)-1H-indol-3-yl)propyl]piperidine;

4-benzyloxy-1-[2-fluoro-3-(5-(1,2,4-triazol-4-yl)-1H-indol-3-yl)propyl]piperidine;

4-benzyloxy-1-[2,2-difluoro-3-(5-(1,2,4-triazol-4-yl)-1H-indol-3-yl)propyl]piperidine;

and salts and prodrugs thereof.

8. A pharmaceutical composition comprising an effective amount of a compound of formula I as defined in claim 1 or a pharmaceutically acceptable salt thereof or a prodrug thereof in association with a pharmaceutically acceptable carrier.

9. A process for the preparation of a compound as claimed in claim 1, which comprises:

(A) reacting a compound of formula III:

(III)

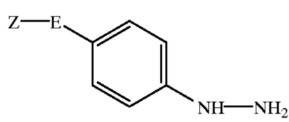

wherein Z and E are as defined in claim 1; with a compound of formula IV, or a carbonyl-protected form thereof:

(IV)

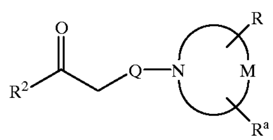

wherein $R^2$, Q, M, R and $R^a$ are as defined in claim 1; followed, where required, by N-alkylation by standard methods to introduce the moiety $R^3$; or (B) reacting a compound of formula VII:

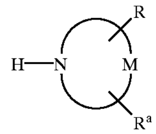

wherein R and $R^a$ are as defined in claim 1; with a compound of formula VIII:

(VIII)

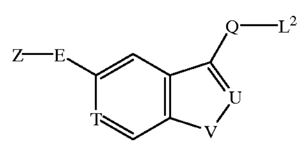

wherein Z, E, Q, T, U and V are as defined in claim 1, and $L^2$ represents a suitable leaving group; or (C) cyclising a compound of formula X:

(X)

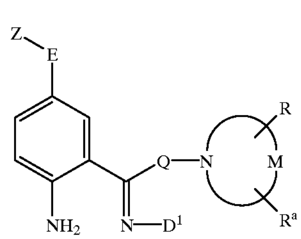

wherein Z, E, Q, M, R and $R^a$ are as defined in claim 1, and $D^1$ represents a readily displaceable group; followed, where required, by N-alkylation by standard methods to introduce the moiety $R^3$; or (D) cyclising a compound of formula XIII:

(XIII)

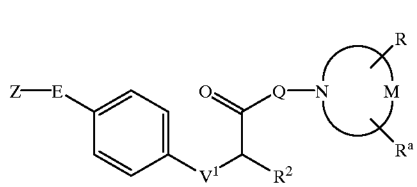

wherein Z, E, Q, $R^2$, M, R and $R^a$ are as defined in claim 1, and $V^1$ represents oxygen or sulphur; or (E) reducing a compound of formula XVI:

(XVI)

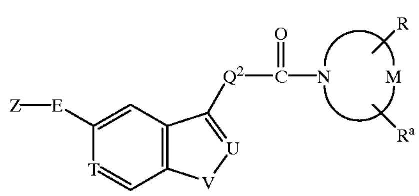

wherein Z, E, T, U, V, M, R and $R^a$ are as defined in claim 1, and —$Q^2$—$CH_2$— corresponds to the moiety Q as defined in claim 1.

10. A compound as claimed in claim 3 wherein $R^{11}$ represents a group of formula —$NR^9R^{10}$.

11. A compound as claimed in claim 4 wherein $R^{11}$ represents a group of formula —$NR^9R^{10}$.

* * * * *